US 6,657,427 B2

(12) United States Patent
ÅAkerblom

(10) Patent No.: US 6,657,427 B2
(45) Date of Patent: Dec. 2, 2003

(54) METHOD AND DEVICE FOR MEASURING A DISTANCE BETWEEN A STATOR AND A ROTOR

(75) Inventor: Bengt ÅAkerblom, Vårby (SE)

(73) Assignee: D/A Production AB, Skarholmen (SE)

( * ) Notice: Subject to any disclaimer, the term of this patent is extended or adjusted under 35 U.S.C. 154(b) by 0 days.

(21) Appl. No.: 09/979,143

(22) PCT Filed: Mar. 20, 2001

(86) PCT No.: PCT/SE01/00572

§ 371 (c)(1),
(2), (4) Date: Nov. 20, 2001

(87) PCT Pub. No.: WO01/71276

PCT Pub. Date: Sep. 27, 2001

(65) Prior Publication Data

US 2002/0158628 A1 Oct. 31, 2002

(30) Foreign Application Priority Data

Mar. 23, 2000 (SE) .................................................. 0001031

(51) Int. Cl.$^7$ .................................................. G01B 7/14
(52) U.S. Cl. .............................. 324/207.26; 324/207.15
(58) Field of Search ................ 324/207.26, 207.11, 324/202, 207.13, 207.12, 229, 243, 242, 239, 227, 226, 207.15; 241/37, 30; 73/660, 661

(56) References Cited

U.S. PATENT DOCUMENTS

| 3,434,670 A | * | 3/1969 | May | 241/37 |
|---|---|---|---|---|
| 3,848,814 A | * | 11/1974 | Syrjanen | 241/37 |
| 3,898,562 A | | 8/1975 | Mizikar et al. | 324/758 |
| 4,454,991 A | * | 6/1984 | Brenholdt | 241/30 |
| 4,627,578 A | | 12/1986 | Whyte | 241/30 |
| 4,727,322 A | | 2/1988 | Lonchampt et al. | 324/229 |
| 4,820,980 A | * | 4/1989 | Dodson-Edgars | 324/207.24 |
| 4,878,020 A | | 10/1989 | Kärnä et al. | 324/207.17 |
| 5,691,636 A | | 11/1997 | Allshouse et al. | 324/207.15 |

FOREIGN PATENT DOCUMENTS

SE         401 896         6/1978

* cited by examiner

Primary Examiner—N. Le
Assistant Examiner—Reena Aurora
(74) Attorney, Agent, or Firm—Young & Thompson

(57) ABSTRACT

In a machine which is provided with a stator and an opposite rotor, a sensor of magnetic type, arranged in the stator, for determining the distance between the stator and the rotor can be calibrated by the sensor first being moved relative to the stator into contact with the rotor for zeroing. The sensor is then reversed a predetermined distance, after which the sensor signal can be used for determining the distance between the stator and the rotor. In an arrangement suitable for the purpose, the stator has at least one sensor of magnetic type, which is intended to interact with an opposite surface on the rotor. The sensor is mounted displaceably in the axial direction of the rotor and can be brought into contact with the rotor.

8 Claims, 1 Drawing Sheet

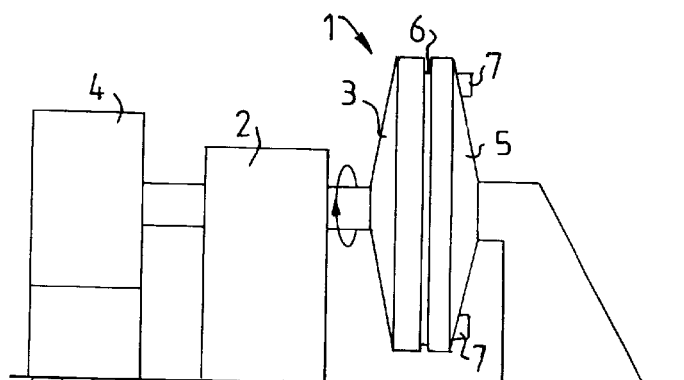
FIG. 1
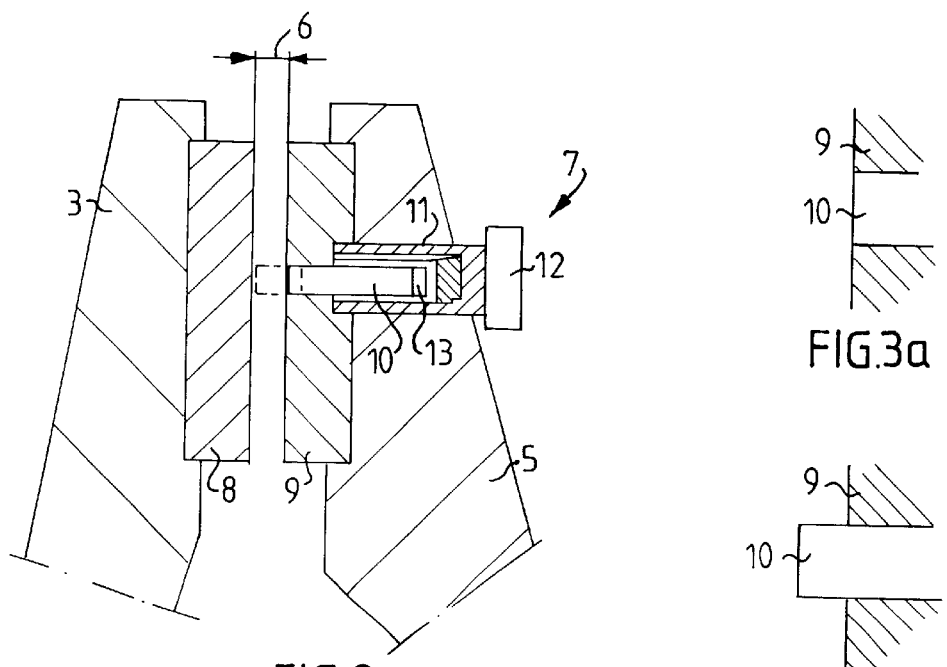
FIG. 2
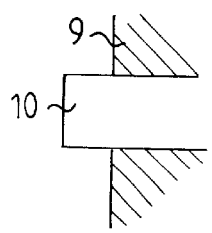
FIG. 3a
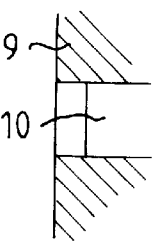
FIG. 3b
FIG. 3c
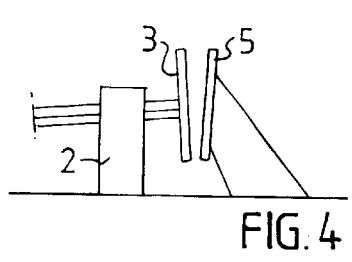
FIG. 4

METHOD AND DEVICE FOR MEASURING A DISTANCE BETWEEN A STATOR AND A ROTOR

TECHNICAL FIELD

The present invention relates on the one hand to a method for determining distance, and on the other hand to an arrangement for determining distance.

PRIOR ART

In refiners intended for paper pulp production, the size of the refining gap between a stator and a rotor is changed during operation as a consequence of wear on the mutually facing refining segments on the stator and the rotor. For reasons of quality, it is desirable to have good control over the size of the refining gap and to be able to compensate for wear, or to change the size of the refining gap for other reasons. Refiners of this type usually have long operating periods, often several months, or which reason it should be possible to effect monitoring of the size of the refining gap during operation.

In order to measure the size of the refining gap, it is customary to use sensors of magnetic type which are positioned in a stationary manner in the stator, with the end surface of the measuring head level with the surface of the refining segments. For sensor calibration, the rotor is first, while rotating and during idle running, moved axially in the direction towards the stator until the refining segments on the two come into contact with one another. In this state, the sensor is zeroed. By then reversing the rotor a predetermined distance, the sensor can be calibrated.

One of the disadvantages of such a procedure is that it can DC used only on machines in which the rotor can be operated very accurately, as otherwise the zeroing wear can be great, and calibration and checking of the sensor can furthermore be carried out only during idle running. Another disadvantage is that the positioning of the sensor in the surface of the refining segments results in continuous wear of the sensor during operation.

THE OBJECT OF THE INVENTION

The object of the invention is to make easier and more reliable determination of the distance between the stator and the rotor possible in machines of the type indicated.

SUMMARY OF THE INVENTION

By using at least one sensor mounted movably in the stator, the sensor can be calibrated easily with regard to gain. Moreover, the possibility is afforded of checking the sensor by moving it a certain distance, with the rotor either at a standstill or rotating. For zero calibration, it is no longer necessary to move the rotor axially until contact is made between the refining segments, but it is sufficient to move the sensor into contact with the rotor.

The mobility of the sensor also makes it possible, in the event of contact between the refining segments on the rotor and the stator during operation, to reverse the sensor a little distance from its normal position level with the surface of the refining segment, so that further wear of the sensor is avoided. By using a number of sensors on the stator, it is also possible to measure and control any relative inclination between the stator and the rotor.

Further features and advantages of the solution according to the invention emerge from the description and the claims.

The invention will be described in greater detail below with references to exemplary embodiments shown in the drawings.

DESCRIPTION OF THE FIGURES

In the drawing:

FIG. 1 shows a diagrammatic view of a machine provided with an arrangement according to the invention, FIG. 2 shows a detail of a sensor mounting in the stator on a machine according to FIG. 1, FIG. 3 shows a diagrammatic view of a sensor in different positions in a stator, and FIG. 4 shows a diagrammatic view of a machine displaying inclination between the stator and the rotor.

DESCRIPTION OF EXEMPLARY EMBODIMENTS

FIG. 1 shows diagrammatically those parts of a machine 1 of the refiner type intended for paper pulp production which are necessary to understand the invention. This machine is provided with a rotor 3 which is mounted rotatably in a stand 2, is driven by a motor 4 and can also be moved axially in the direction towards and away from a stator 5 in order to regulate the size of a refining gap 6 between the rotor 3 and the stator 5. For checking the size of the refining gap 6, at least one sensor arrangement 7, with a sensor of magnetic type which suitably works according to the reluctance principle, is mounted in the stator 5. This type of sensor is well known to the expert in the field. Two or more sensor arrangements 7 can suitably be distributed around the stator 5.

As shown in greater detail in FIG. 2, both the rotor 3 and the stator 5 are provided with refining segments 8, 9 which have a surface suitable for refining paper pulp and are mounted in a suitable number in a ring on the rotor and the stator. These refining segments 8, 9 are subjected to wear during operation and are therefore suitably replaceable mounted. In at least one of the refining segments 9, the stator 5 is provided with a sensor arrangement 7, in which a sensor 10 is mounted axially displaceably in a housing 11 which is mounted in a fixed manner in the stator 5 and can be, for example, screwed into the stator. The bearing between the sensor 10 and the housing 11 can be of, for example, the ballscrew type with small pitch, where a given rotation of an operating means 12 produces a given axial displacement of the sensor 10 in either direction. The operating means 12 can consist of, for example, a wheel, but it is also possible to use, for example, an electric stepping motor or servomotor in order for it to be possible to effect operation at a distance from the stator 5.

For calibration of the sensor 10, zeroing is carried out first by the sensor being moved into contact with the refining segment 8 on the rotor 3 which, in this connection, is rotating. In order to make it possible to establish reliably when contact is made between the end of the sensor 10 (shown by a broken line in FIG. 2) and the refining segment 8 on the rotor 3, use can be made of, for example, an accelerometer 13 arranged on the sensor 10. This accelerometer registers the vibrations which occur on contact and emits a corresponding signal, which makes it possible to interrupt the feed of the sensor 10 in time. If appropriate, the accelerometer 13 can be coupled to a stepping motor forming part of the sensor arrangement 7, so that the motor interrupts the feed automatically when a suitable signal is supplied. The signal obtained from the sensor 10 in this contact position then represents the zero position of the sensor. By subsequently reversing the sensor 10 a predetermined distance, a new signal is obtained, which represents the distance covered. In this way, the sensor is calibrated.

FIG. 3 shows in greater detail the relative location of the sensor 10 and the refining segment 9 in different positions of the sensor 10. The position shown in FIG. 3a, in which the end of the sensor is level with the surface of the refining segment, constitutes the normal working position of the sensor. The position shown in FIG. 3b, in which the sensor extends outside the refining segment, is used, as mentioned, for zero calibrating the sensor. The position shown in FIG. 3c, lastly, in which the sensor is located slightly inside the surface of the refining segment, can be used to spare the sensor when contact between the rotor and the stator has occurred during operation.

In a machine 1 of the type described here, the rotor and the stator usually have a rather large diameter, often of the order of roughly 1.5–2 m, and the rotor 3 usually rotates at a speed of the order of roughly 1500–1800 rpm. Even relatively minor bearing faults can therefore easily result in inclination between the rotor and the stator of the type shown diagrammatically in FIG. 4. It is therefore important that both base mounting and bearing are stable so as to obtain good parallelism between the rotor and the stator, so that the gap 6 has the same size overall. By using a number of suitably positioned sensor arrangements 7 designed according to the invention, this can be checked, even during operation. In this connection, it is suitable to use three such sensor arrangements 7 which are positioned in a mutually spaced manner in the circumferential direction of the stator 5. If appropriate, use can be made of only two diametrically positioned sensor arrangements 7 if inclination between the rotor and the stator can be expected to occur in only a certain plane.

The gap 6 usually has a size of roughly 0.30–1.50 mm. As the refining segments 8, 9 can be worn down at such a rate that rotor movement of roughly 2 mm/2000 h is necessary in order to maintain the gap size, it is obvious that good measuring accuracy is desirable in order for it to be possible to make suitable corrections during operation for the purpose of maintaining a certain product quality.

What is claimed is:

1. Method for, in a machine provided with a stator (5) and an opposite rotor (3), calibrating a sensor (10), arranged in the stator (5), for measuring the distance between the stator and the rotor, the sensor being of magnetic type, and zeroing of the sensor being performed by bringing the sensor (10) and the rotor (3) into contact with one another and reading the signal then obtained from the sensor during the rotation of the rotor, after which the sensor and the rotor are moved a predetermined distance apart from one another, and the signal then obtained is used as an indication of this distance, in which way the sensor signal can be used for determining the distance between the stator and the rotor, characterized in that, for zeroing and calibration, the sensor (10) is moved axially relative to the stator (5), while the axial position of the rotor (3) is kept unchanged relative to the stator (5).

2. Method according to claim 1, characterized in that, for determining distance during operation of the machine, the end surface of the sensor (10) is kept level with or inside that end surface of the stator (5) facing the rotor (3).

3. Method according to claim 1, characterized in that, for zeroing the sensor (10), a signal from an accelerometer (13) arranged on the sensor (10) is used in order to establish when contact occurs between the sensor (10) and the rotor (3).

4. Method according to claim 1, characterized in that at least three sensors (10) are used, which are positioned in a mutually spaced manner in the circumferential direction of the stator (5).

5. Arrangement for determining the distance between a stator (5) and a rotating rotor (3) opposite the stator in a machine, in particular a refiner intended for paper pulp production, the stator (5) being provided with at least one sensor (10) of magnetic type, which is intended to interact with an opposite surface on the rotor, characterized in that the sensor (10) is mounted movably in the stator (5) and is displaceable in the axial direction of the rotor (3), in which connection it, for defining a zero position and for calibration is movable so far out from the stator that it can be brought into contact with the rotor (3) when the rotor is rotating at a distance from the stator.

6. Arrangement according to claim 5, characterized in that the sensor (10) forms part of a sensor arrangement (7) which is mounted in the stator (5) and also includes an operating means (12) for moving the sensor.

7. Arrangement according to claim 5, characterized in that the operating means (12) consists of an electric stepping motor.

8. Arrangement according to claim 5, characterized in that a means, suitably an accelerometer (13), is arranged on the sensor (10), for indicating contact between the sensor (10) and the rotor (3) when these are brought towards one another for zero calibration of the sensor.

* * * * *